(12) United States Patent
Costa et al.

(10) Patent No.: US 8,337,737 B2
(45) Date of Patent: Dec. 25, 2012

(54) METHOD OF MAKING A PISTON FOR A DISPENSER

(75) Inventors: Steven G. Costa, Rumford, RI (US); David J. Dunlap, Rehoboth, MA (US)

(73) Assignee: Nordson Corporation, Westlake, OH (US)

( * ) Notice: Subject to any disclaimer, the term of this patent is extended or adjusted under 35 U.S.C. 154(b) by 1 day.

(21) Appl. No.: 13/005,689

(22) Filed: Jan. 13, 2011

(65) Prior Publication Data

US 2011/0101563 A1 May 5, 2011

Related U.S. Application Data

(62) Division of application No. 11/760,984, filed on Jun. 11, 2007, now Pat. No. 7,891,528.

(60) Provisional application No. 60/806,486, filed on Jul. 3, 2006.

(51) Int. Cl.
*B29C 45/14* (2006.01)
*B29C 45/16* (2006.01)
(52) U.S. Cl. .................. 264/250; 264/255; 264/274
(58) Field of Classification Search ............... None
See application file for complete search history.

(56) References Cited

U.S. PATENT DOCUMENTS

| 3,036,874 | A | | 5/1962 | Sharp |
| 3,057,630 | A | | 10/1962 | Sneed |
| 4,201,209 | A | * | 5/1980 | LeVeen et al. ............ 604/218 |
| 4,385,025 | A | * | 5/1983 | Salerno et al. ............ 264/255 |
| 5,577,641 | A | | 11/1996 | De Laforcade et al. |
| 5,695,465 | A | | 12/1997 | Zhu |
| 5,902,276 | A | | 5/1999 | Namey, Jr. |
| 6,004,300 | A | | 12/1999 | Butcher et al. |
| 6,585,700 | B1 | | 7/2003 | Trocki et al. |
| 6,817,990 | B2 | * | 11/2004 | Yap et al. ............ 604/228 |
| 2005/0029306 | A1 | | 2/2005 | Brennan |

(Continued)

FOREIGN PATENT DOCUMENTS

EP 0375778 A1 7/1990

(Continued)

OTHER PUBLICATIONS

European Patent Office, International Search Report and Written Opinion in PCT Application Serial No. PCT/US2007/070839, Jan. 2, 2008.

(Continued)

*Primary Examiner* — Edmund H. Lee
(74) *Attorney, Agent, or Firm* — Wood, Herron & Evans, L.L.P.

(57) ABSTRACT

A dispenser for dispensing a liquid onto a substrate includes a dispenser body having an output and a reservoir in fluid communication with the output, the reservoir being defined by a wall and adapted to hold a supply of liquid to be dispensed. A piston is disposed in the reservoir and adapted to pressurize the liquid so that an amount of liquid is dispensed from the output of the dispenser. The piston includes a base portion having an outer periphery and having a first hardness, and a skirt portion integrally molded to the outer periphery of the base portion and having a second hardness lower than the first hardness. A two-shot molding operation may be used to form the piston with the base portion being, for example, formed in the first shot of the molding operation and the skirt portion being formed in the second shot of the molding operation.

10 Claims, 8 Drawing Sheets

U.S. PATENT DOCUMENTS

2007/0000951 A1   1/2007   Sprinhorn

FOREIGN PATENT DOCUMENTS

| EP | 1132146 | A2 | 9/2001 |
| WO | 79-01111 | A1 | 12/1979 |
| WO | 93/17954 | A1 | 9/1993 |
| WO | 01/60434 | A1 | 8/2001 |

OTHER PUBLICATIONS

European Patent Office, Invitation to Pay Additional Fees in PCT Application Serial No. PCT/US2007/070839, Nov. 2, 2007.

* cited by examiner

METHOD OF MAKING A PISTON FOR A DISPENSER

CROSS REFERENCE TO RELATED APPLICATIONS

This application is a divisional of application Ser. No. 11/760,984, filed Jun. 11, 2007, now U.S. Pat. No. 7,891,528, which claims benefit of Provisional Application Ser. No. 60/806,486 filed on Jul. 3, 2006 (expired), the disclosures of which are expressly incorporated by reference herein in their entirety.

TECHNICAL FIELD

This invention is generally related to liquid dispensers for dispensing liquid and, more particularly, to pistons in liquid dispensers and methods of making the same.

BACKGROUND

Various types of dispensers are used in many industries for placing liquids, such as adhesives, conformal coating materials, solder paste, solder flux, and other such materials, onto substrates during an assembly process. One such type of liquid dispenser is a syringe-type of dispenser having a dispenser body defining a barrel reservoir for holding a supply of liquid material to be dispensed. A dispensing tip may be coupled to the syringe at one end thereof and in fluid communication with the reservoir. A piston is disposed in the reservoir and is movable therein to pressurize the liquid in the reservoir so as to dispense a small amount of liquid from the dispensing tip and onto a substrate or the like.

Industrial applications may require that the liquid be dispensed in very precise volumes and at precise locations. To this end, liquid dispensers may include one or more actuators for moving the piston within the reservoir in a controllable and predictable manner. For instance, pneumatic actuators are known that use compressed air applied to the piston to move the piston and dispense liquid from the dispenser. Those of ordinary skill in the art will recognize that other type of actuators, such as linear actuators, may be used to control movement of the piston within the reservoir. In applications where such precise dispensing is not required, the piston may be moved through a manual process.

While such dispensing systems are widely used throughout industry and are successful for their intended purposes, users and manufacturers of these dispensing systems continually strive to improve their design and operation. For instance, in some applications current dispensing systems have some drawbacks. By way of example, in some instances dispensing one-part epoxies in such dispensers encounter premature curing of the epoxy while in the dispenser, which in turn locks up the dispenser and prevents its proper operation. The one-part epoxies may include microspheres of a catalyzing agent or hardener such that when the microspheres are burst or ruptured, the epoxy begins to cure. In normal operation, the epoxy may be dispensed onto a substrate and the microspheres subsequently ruptured through mixing or other mechanical action to cause curing of the epoxy. For instance, pre-applied thread lockers use one-part epoxies where the engagement between the threaded members causes rupture of the microspheres and curing of the epoxy.

Dispensers may utilize a piston that is formed from a relatively hard or rigid material, such as polyethylene. The rigid material of the piston reduces deformation of the piston when pressure or forces are applied thereto and may thus permit relatively accurate and precise liquid dispensing. When used for one-part epoxies, however, contact between the relatively hard piston and the microspheres may be sufficient to rupture the microspheres and cause curing of the epoxy in the dispenser. In this case, the dispenser may have to be discarded, which increases waste and thus increases costs.

The formation of the piston from a relatively hard material also has other drawbacks, such as sealing between the piston and the wall of the reservoir. In some applications, when manufacturing facilities are shut down or otherwise not in operation, activated or pre-mixed adhesives will often be frozen or cooled to extend their pot life and reduce the amount of adhesive discarded. Thus, the dispenser may be placed in a freezer or refrigerator to cool the adhesive and slow reaction rates. Once manufacturing recommences, the adhesives will be thawed and put back into operation. Such cooling/freezing of the dispenser may permit air to leak past the piston and into the reservoir. When the dispenser is thawed and put back in operation, the air may become entrained in the liquid causing burping or sputtering as the liquid is dispensed. Products may consequently have to be discarded, which increases waste product and increases costs.

In addition to issues discussed above, pressures developed in the reservoir during dispensing may, in some cases, be sufficient to overcome the seal between the relatively hard piston and the wall of the reservoir such that liquid may leak past the piston. Accordingly, there is a need for an improved dispenser and a method for making the same that addresses these and/or other issues of known dispensers.

SUMMARY

In one embodiment, a piston for a dispenser adapted to dispense a liquid onto a substrate includes a base portion having an outer periphery and having a first hardness, and a skirt portion coupled to the outer periphery of the base portion and having a second hardness that is lower than the first hardness. By way of example, the base portion may have a durometer hardness of about 65 Shore D or greater. The base portion may include polyethylene or polypropylene, for example. The skirt portion may have a durometer hardness of about 55 Shore D or less. The skirt portion may include a thermoplastic elastomer, a silicone based rubber, a fluoroelastomer, an ethylene-propylene rubber, buna-N, or combinations thereof, for example.

In another embodiment, a dispenser for dispensing a liquid onto a substrate includes a dispenser body having an output and a reservoir in fluid communication with the output. The reservoir includes a wall at least partially defining the reservoir and adapted to hold a supply of liquid to be dispensed. A piston is disposed in the reservoir and is configured to pressurize the liquid so that an amount of the liquid is dispensed from the output of the dispenser body. The piston includes a base portion having an outer periphery and having a first hardness, and a skirt portion coupled to the outer periphery of the base portion and having a second hardness that is lower than the first hardness. The piston is configured to contact the wall along at least a portion of the skirt portion.

In yet another embodiment, a method of making a piston for a dispenser adapted to dispense a liquid onto a substrate includes molding a base portion of the piston by injecting a first curable material in a first shot of a molding operation. A skirt portion is molded to the base portion by injecting a second curable material during a second shot of the molding operation. The first curable material may have a first hardness and the second curable material may have a second hardness that is lower than the first hardness.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
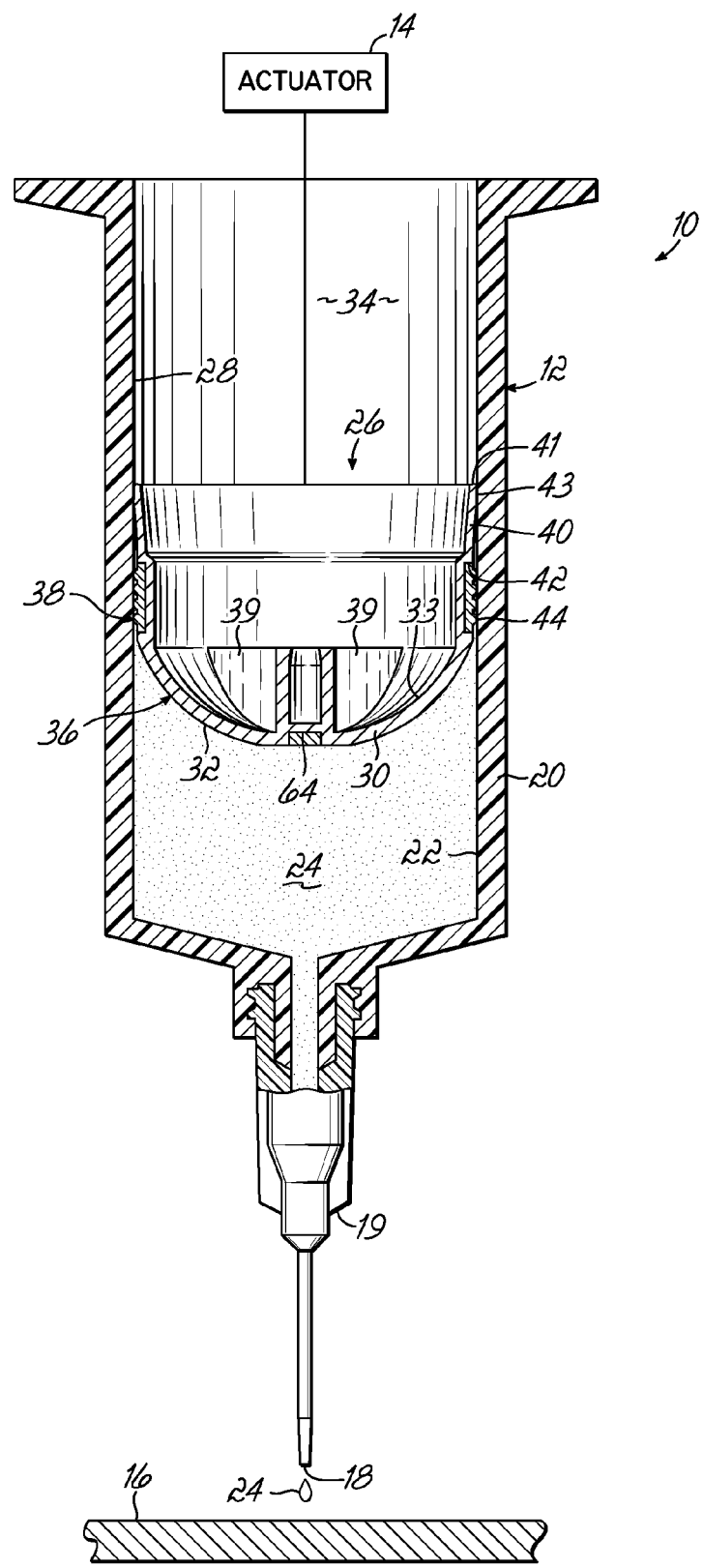
FIG. 1 is a cross-sectional view of a dispenser in accordance with one embodiment.

Referring to the figures and, more particularly to FIG. 1, an embodiment of a dispensing system 10 for dispensing liquid materials such as adhesives, conformal coating materials, solder paste, solder flux, and other such materials, includes a liquid dispenser 12 and a diagrammatically depicted actuator 14 for dispensing the liquid from dispenser 12 and onto a substrate 16 positioned proximate the dispenser 12. The actuator 14 may be formed as an integral part of the dispenser 12 or may be separate and operatively coupled to the dispenser 12. As shown in the drawings, in one embodiment, the liquid dispenser 12 may be configured as a syringe-type of dispenser that may be actuated to dispense liquid from an output 18 in the form of an orifice of dispenser 12, such as through dispensing tip 19. To this end, liquid dispenser 12 includes a dispenser body 20 or barrel that defines a reservoir 22 for holding a liquid 24 to be dispensed. A movable piston 26 is disposed in the reservoir 22 and is operatively coupled to the actuator 14 such that when actuated, the piston 26 pressurizes the liquid 24 in reservoir 22 and causes liquid 24 to flow from reservoir 22, through output 18 of dispensing tip 19, and onto substrate 16. While liquid dispenser 12 is shown as having the reservoir 22 disposed within dispenser body 20, those of ordinary skill in the art will recognize that the reservoir may be located external to dispenser body 20 but in fluid communication with dispenser body 20 for dispensing the liquid through the output 18.

The piston 26 is sized to closely fit within reservoir 22 so as to create a seal between an outer periphery of the piston 26 and the interior wall 28 of dispenser body 20. The seal between the piston 26 and the interior wall 28 is adapted to prevent or minimize the likelihood of any liquid 24 in reservoir 22 leaking past or by the piston 26. As mentioned above, piston 26 is operatively coupled to actuator 14 for pressurizing the liquid 24 in reservoir 22 and causing the liquid 24 to be dispensed through output 18. In one embodiment, the actuator 14 may be a pneumatic actuator that uses compressed air to pressurize a chamber 34 above the piston 26. The air pressure then moves the piston 26 so as to dispense the liquid 24 from dispensing tip 19. In another embodiment, the actuator 14 may be a linear actuator utilizing servo or stepping motors to displace the piston 26 within reservoir 22 and dispense the liquid 24 from dispensing tip 19. In yet another embodiment, the piston 26 may be moved in reservoir 22 through a manual process to dispense the liquid 24 from the dispensing tip 19. Those of ordinary skill in the art will readily appreciate other types of actuators that may be alternatively used to move piston 26 within reservoir 22 so as to dispense the liquid 24 from the dispensing tip 19.

Figure 2A:
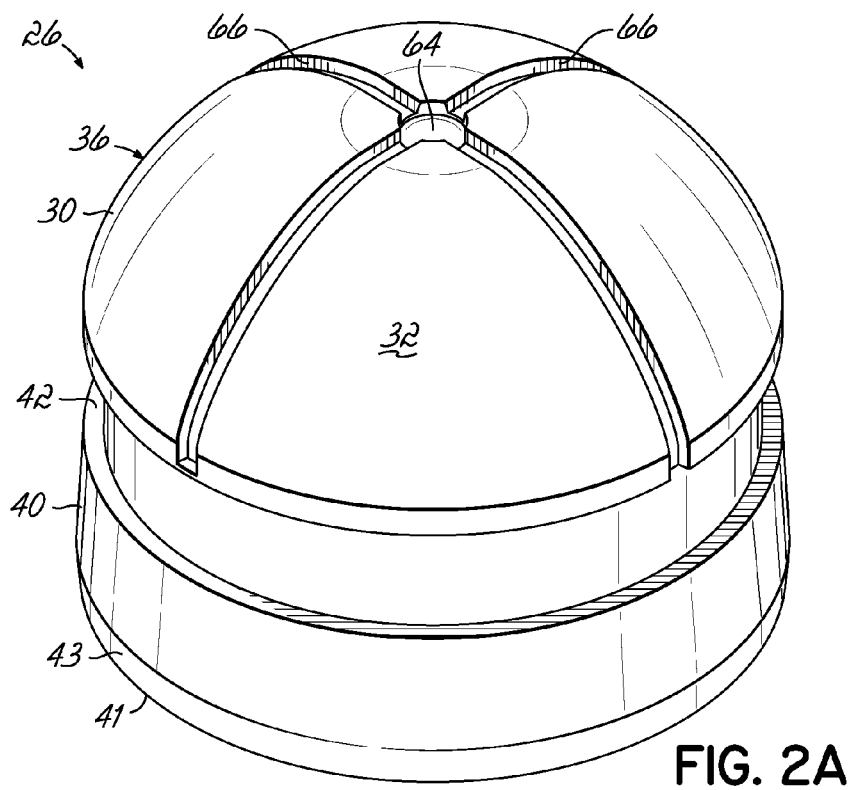
FIG. 2A is a perspective view of the piston shown in the dispenser of FIG. 1.
Figure 2B:
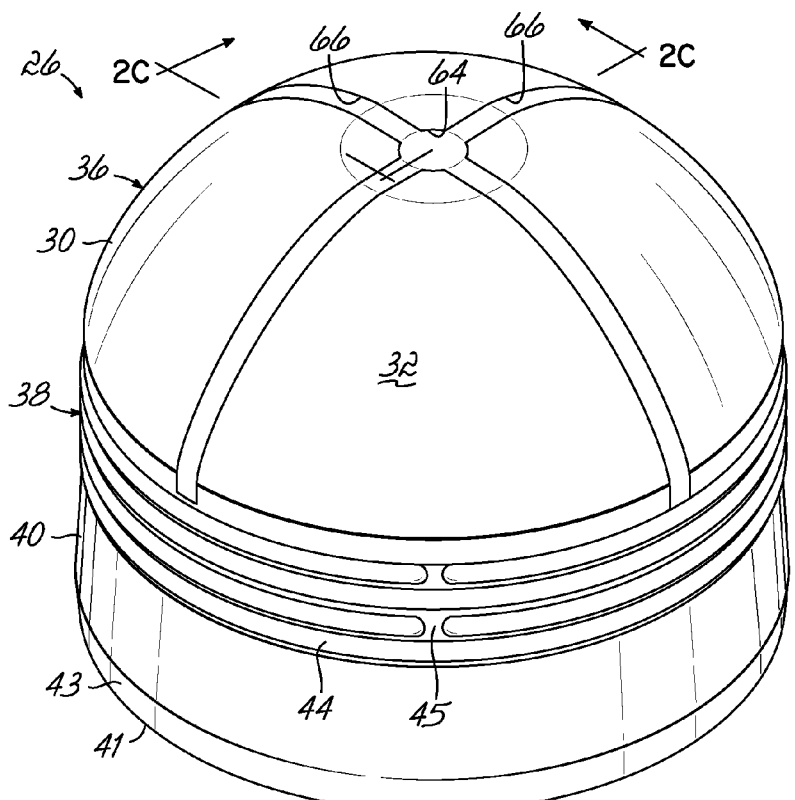
FIG. 2B is a perspective view similar to FIG. 2A showing a skirt portion.
Figure 2C:
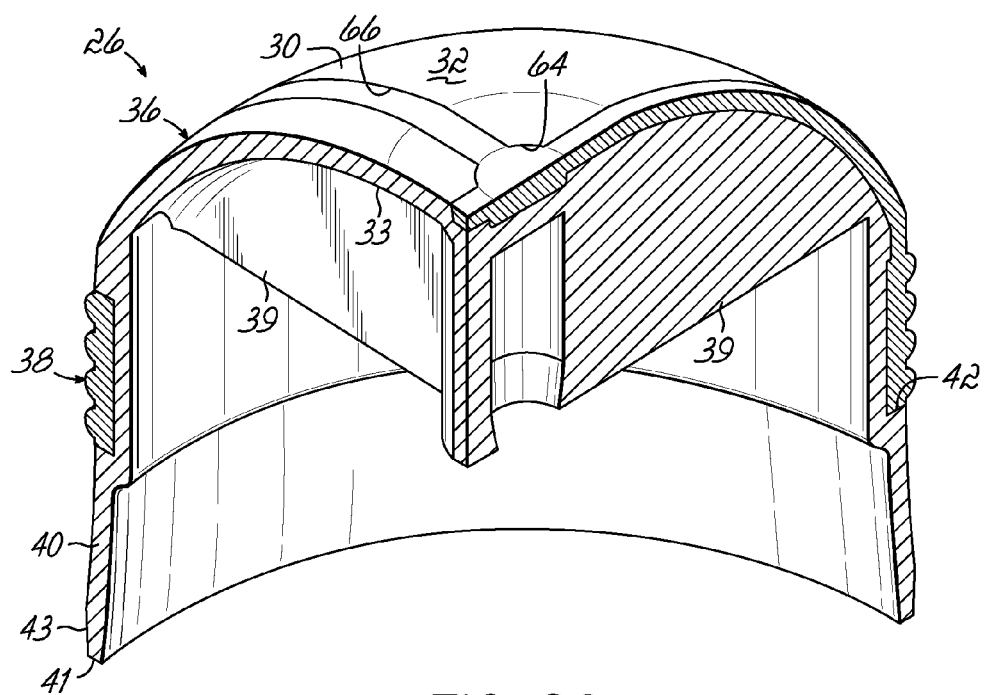
FIG. 2C is a cross-sectional view of the piston along line 2C-2C of FIG. 2B.

With reference to FIGS. 2A-2C, an exemplary embodiment of the piston 26 includes a two-part construction. More particularly, the piston 26 includes a base portion 36 and an outer skirt portion 38. As shown in FIG. 2A, base portion 36 includes an arcuately-shaped head portion 30 having an outer surface 32 adapted to face and contact the liquid 24 in reservoir 22 (FIG. 1), and an inner surface 33 opposite outer surface 32. A generally tubular sidewall 40 defines an outer periphery of base portion 36. The sidewall 40 includes a circumferential groove 42 that receives skirt portion 38 therein. In this embodiment, skirt portion 38 may be configured as one or more generally circumferential rings 44 coupled along the outer periphery of base portion 36. The rings 44 are adapted to extend radially outward from sidewall 40 so as to contact the interior wall 28 defining reservoir 22, at least along a portion thereof. Engagement of the rings 44 with the interior wall 28 provides a seal between the piston 26 and interior wall 28 so as to prevent liquid from leaking by piston 26.

With particular reference to FIG. 2B, one or more of the rings 44 may include one or more gaps 45. The gaps 45 facilitate control on the amount of force required to move the piston 26 relative to the interior wall 28 as determined by the friction between the skirt portion 38 and the interior wall 28. More particularly, the contact area between the skirt portion 38 and the interior wall 28 may be suitably reduced, for example, by increasing the size and/or number of gaps, to thereby reduce the resulting friction acting against motion of the piston 26 relative to interior wall 28. In another aspect of this embodiment, the gaps 45 may provide a tortuous path or labyrinth through the skirt portion 38. For example, and without limitation, the labyrinth may be configured to provide an escape path for any air that is in the reservoir 22 and yet prevent any liquid from escaping past the skirt portion 38. More particularly, the rings 44 may be spaced along groove 42 to provide a relatively small escape path. The escape path may be such that a relatively high pressure is required to move a liquid (e.g., a highly viscous liquid) through the labyrinth while a relatively low pressure is sufficient to allow a gas, such as air, to flow through the labyrinth. Consequently, a gas may be allowed to bleed past the piston 26 via the labyrinth while a liquid is not.

In an exemplary embodiment, the base portion 36 may be made from a material having a first hardness while the skirt portion 38 may be made from a material having a second hardness that is lower than the first hardness. By way of example, the base portion 36 may be made from a material having a durometer hardness of about 65 Shore D or greater or between about 70 and about 80 Shore D. Thus, the base portion 36 may be made of materials that include polyethylene, polypropylene, combination thereof, or other suitably chosen materials. In one aspect of this embodiment, the material for base portion 36 may be a moldable material, such as a moldable polymer. The hardness for base portion 36 may be chosen so as to provide sufficient structural support for the piston 26. In particular, and as noted above, a piston 26 that includes a relatively rigid material may enhance the dispensing of precise amounts (e.g., volumes, weights) of liquid by exhibiting lower levels of deformation during operation.

With particular reference to FIG. 2C, the piston 26 may include one or more ribs 39 on an underside of head portion 30 to provide additional support and rigidity to base portion 36. In one aspect of this embodiment, the ribs 39 may be slightly tapered inwardly in a direction away from head portion 30 (e.g., by about one degree on each side of each of the ribs 39). Moreover, the terminating end 41 of sidewall 40 may include a slight inward taper 43 (e.g., about five degrees), resulting from a molding process used to make the piston 26, as explained in more detail below.

The skirt portion 38 of piston 26 may be made from a relatively soft, compliant material. For example, the skirt portion 38 may be made from a material having a durometer hardness of about 55 Shore D or less or between about 10 and about 50 Shore D. The skirt portion 38 may thus be made of materials including thermoplastic elastomers (TPE), silicone based rubbers, fluoroelastomers such as one commercially available under the tradename Viton®, ethylene-propylene rubber (EPR), buna-N (nitrile), combinations thereof, or other suitably chosen materials. The material for skirt portion 38 may further be a moldable material. A skirt portion 38 made from a material softer than that of the base portion 36 may be advantageous. In one aspect, for example, a relatively soft skirt portion 38 provides a resilient surface that lessens the shock or loads imposed on the liquid 24 by piston 26 as the piston 26 moves within reservoir 22. A softer surface of the skirt portion 38 may be desirable at an interface between the piston 26 and the interior wall 28, where relatively high pressures may be exerted upon the liquid 24 by the piston 26 as piston 26 travels along interior wall 28. In this way, for example, the microspheres of a one-part epoxy within reservoir 22 are less likely to be ruptured, thereby reducing the likelihood of premature curing of the epoxy while in the dispenser 12.

With continued reference to FIGS. 2A-2C, and in another aspect of this embodiment, sealing between the piston 26 and the interior wall 28 is enhanced. In particular, the resiliency of the relatively soft material defining the skirt portion 38 permits the skirt portion 38 to operate as a sealing ring (e.g., an O-ring) capable of being slightly radially compressed against the interior wall 28 to enhance sealing between the piston 26 and the interior wall 28. The seal created between the skirt portion 38 and the interior wall 28 of dispenser body 20 also permits dispenser 12 to be frozen and then thawed without leakage of air around the piston 26 and into the reservoir 22. In particular, the sealing engagement of the skirt portion 38 against the interior wall 28, facilitated by the resiliency of the material defining skirt portion 38, results in a decreased susceptibility to leakage even in light of contractions associated with cooling or freezing of dispenser 12.

In one embodiment, the interior wall 28 may be textured so as to provide an irregular interface between skirt portion 38 and interior wall 28. The texturing may take one of many forms including but not limited to grooves, ridges, bumps, knurls, or combinations thereof. Because the skirt portion 38 conforms to the shape of the interior wall 28, the irregularities provided by the texturing provide an interlocking feature that further enhances the seal between skirt portion 38 and the interior wall 28. The enhanced sealing between the piston 26 and the interior wall 28 prevents air entrainment during freezing/thawing processes as explained above, and may further eliminate or minimize any loss of liquid past the piston 26.

Figure 3A:
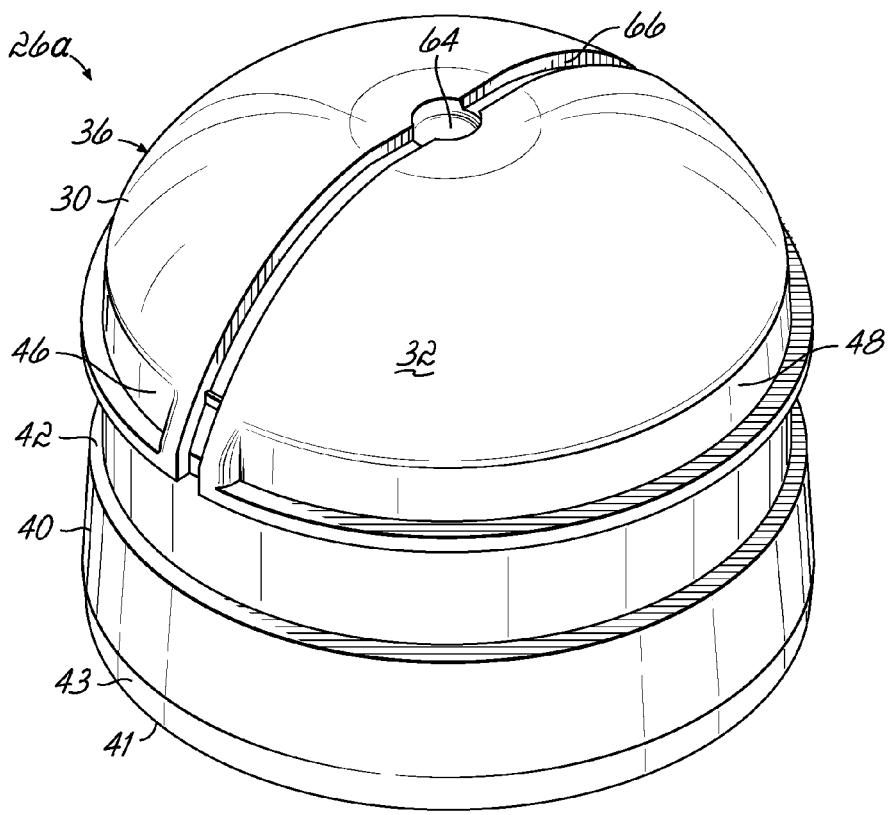
FIG. 3A is a perspective view of another embodiment of a piston.
Figure 3B:
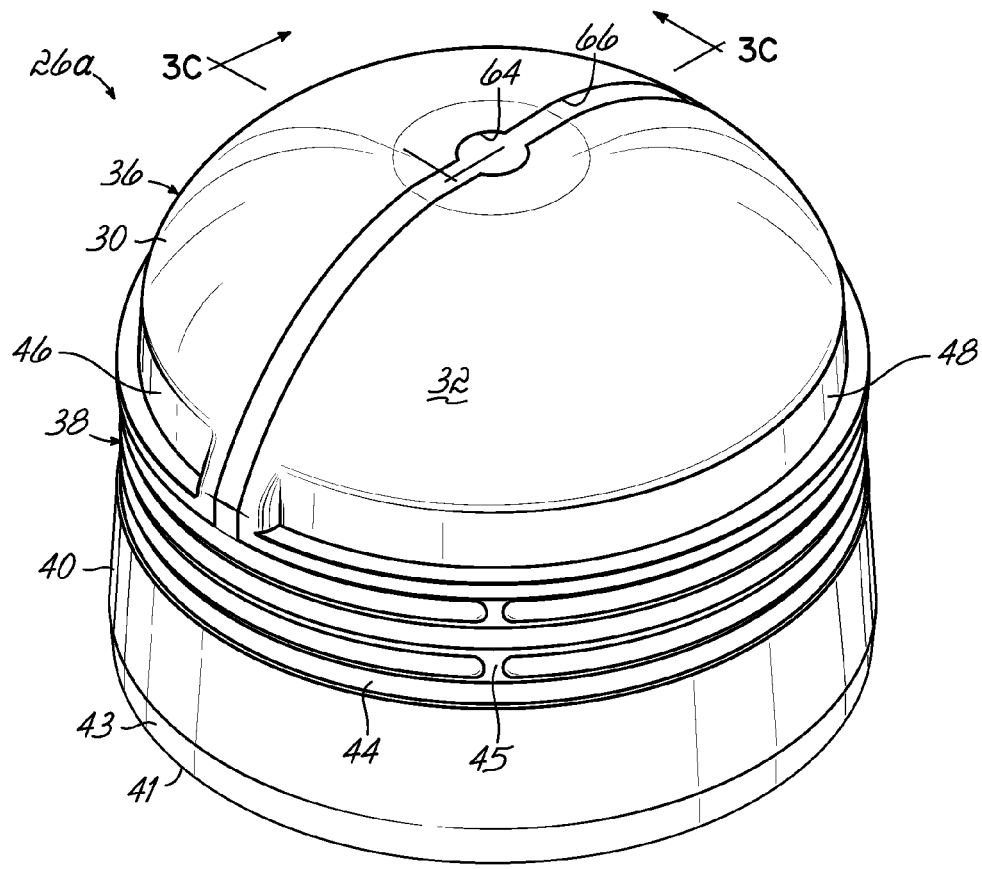
FIG. 3B is a perspective view similar to FIG. 3A including a skirt portion.
Figure 3C:
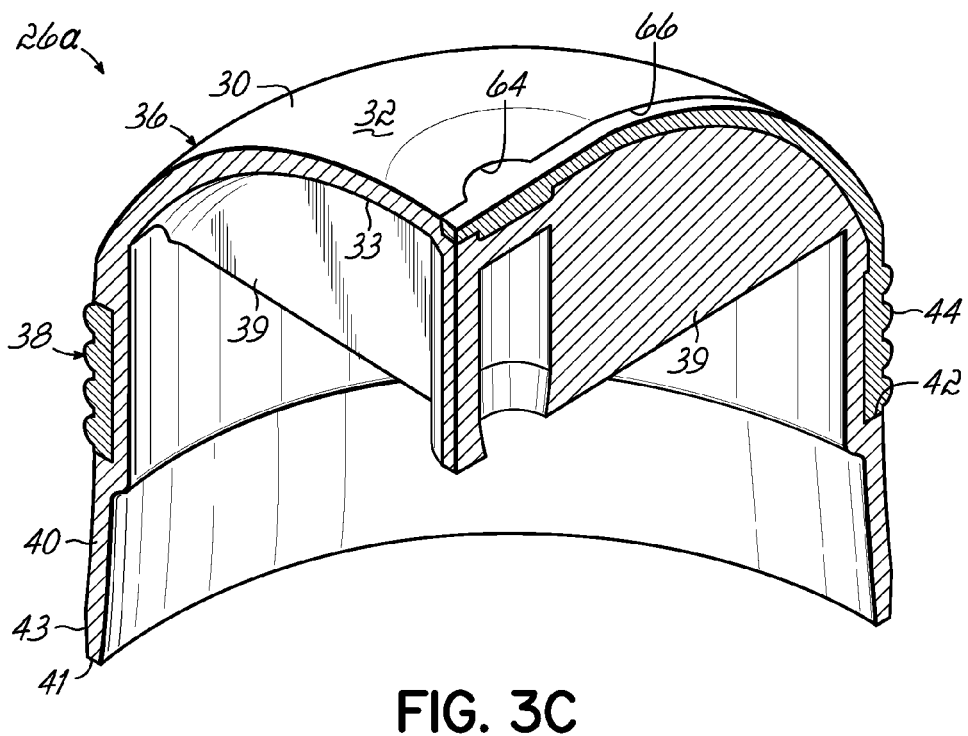
FIG. 3C is a cross-sectional view of the piston along line 3C-3C of FIG. 3B.

With reference to FIGS. 3A-3C, in which like reference numerals refer to like features in FIGS. 2A-2C, another embodiment of a piston 26a is similar in most respects to piston 26 of FIGS. 2A-2C, the description of which may be referred to for an understanding of the piston 26a as well. Piston 26a includes a pair of circumferentially-directed recesses 46, 48 along sidewall 40 and adjacent head portion 30. As appreciated by those of ordinary skill in the art, the recesses 46, 48 prevent or minimize shrinkage of the piston 26a during cooling from a molding process, as discussed in more detail below.

With reference to FIGS. 4A-4D, in which like reference numerals refer to like features in FIGS. 2A-2C, yet another embodiment of a piston 26b is similar in most respects to piston 26 of FIGS. 2A-2C, the description of which may be referred to for an understanding of piston 26b as well. Piston 26b includes a base portion 36 and a skirt portion 38. In this embodiment, the skirt portion 38 is further configured as a lip seal 50. More particularly, the lip seal 50 includes a main body portion 52 that is disposed within groove 42 in sidewall 40 and an extending portion or lip 54 that projects toward head portion 30. The extending portion 54 extends slightly radially outward to define a cavity 56 between the extending portion 54 and the sidewall 40. The extending portion 54 is configured to contact the interior wall 28 and provide enhanced wiping of liquid along interior wall 28.

Figure 4A:
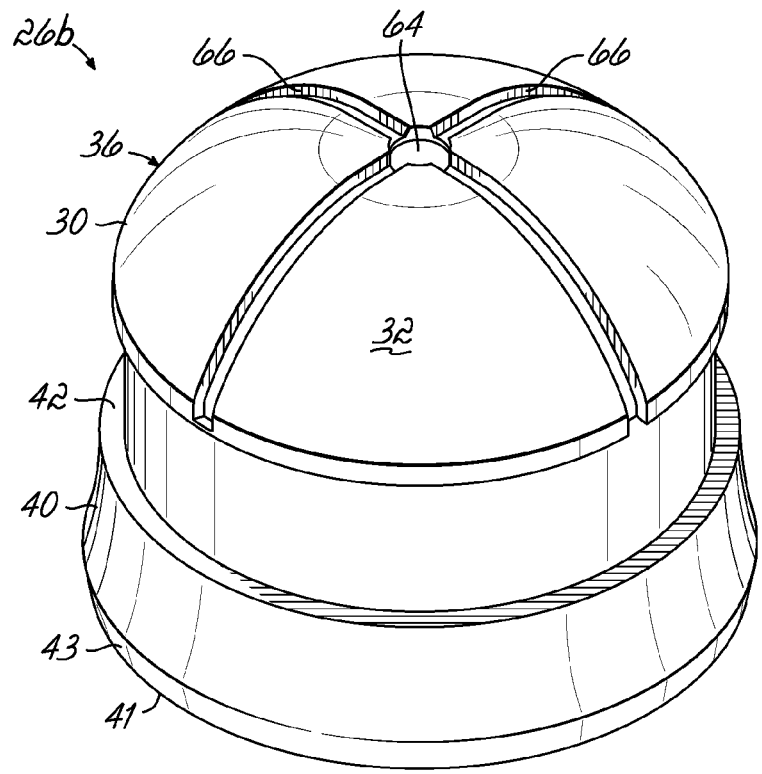
FIG. 4A is a perspective view of another embodiment of a piston.
Figure 4B:
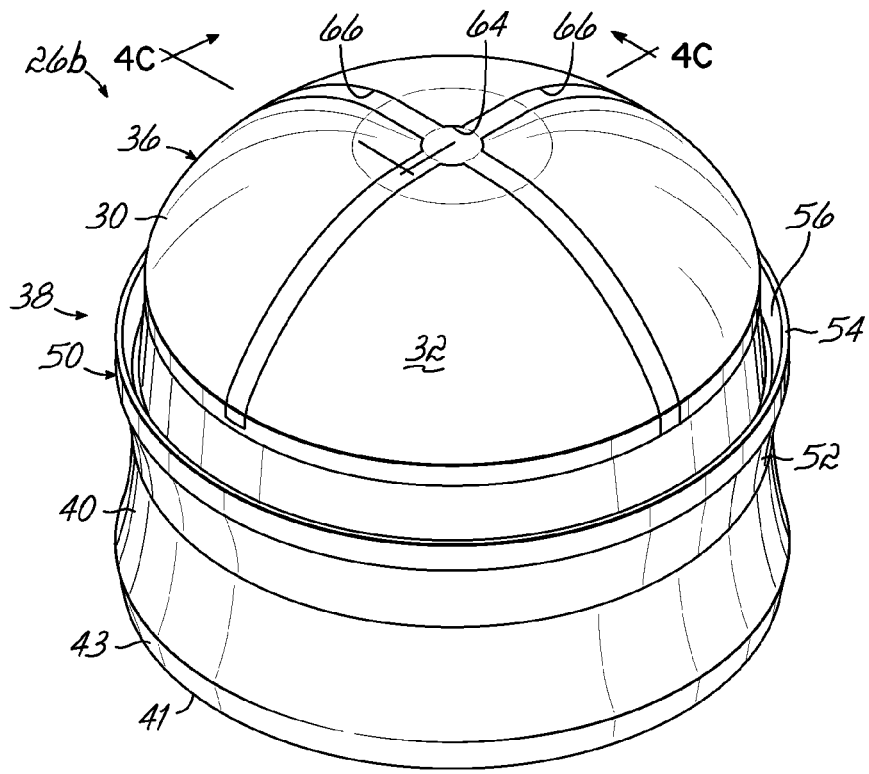
FIG. 4B is a perspective view similar to FIG. 4A including a skirt portion.
Figure 4C:
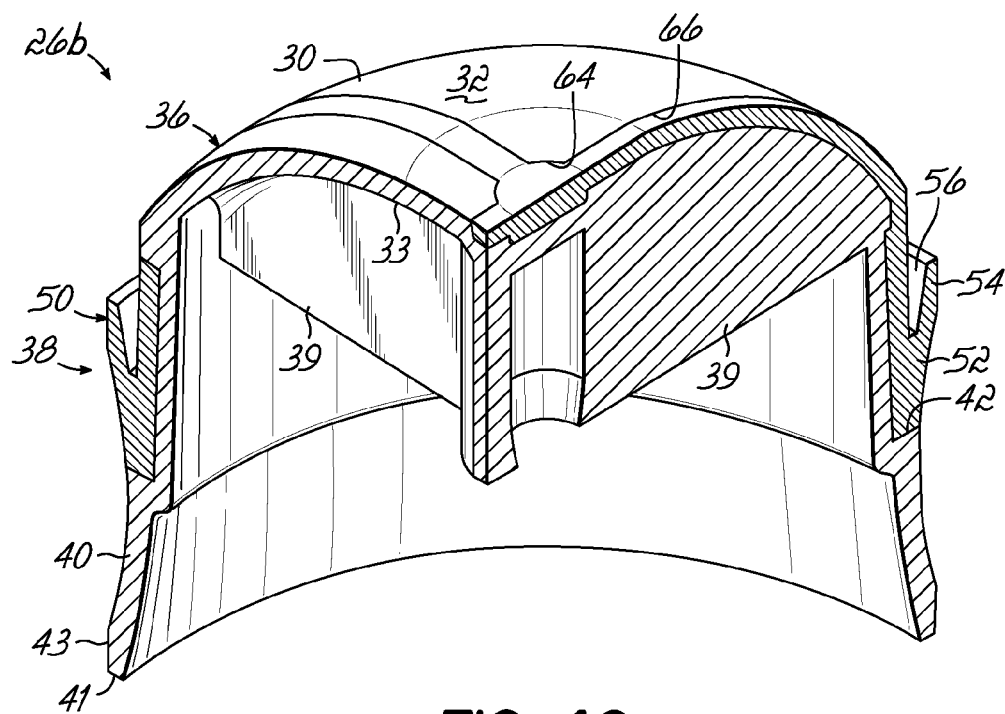
FIG. 4C is a cross-sectional view of the piston along line 4C-4C of FIG. 4B.
Figure 4D:
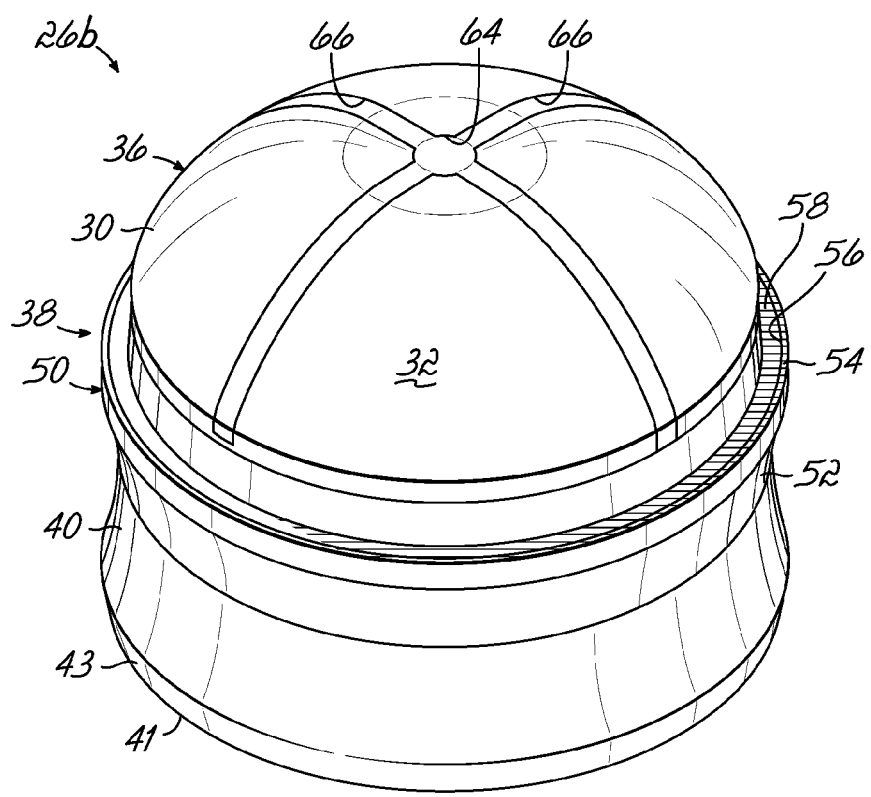
FIG. 4D is a perspective view similar to that shown in FIG. 4B but with a cavity filled with a resilient material.

In one exemplary embodiment, and as shown in FIG. 4D, cavity 56 may be filled with a resilient material 58 that effectively operates as a spring or biasing member. In particular, the resilient material 58 biases the extension portion 54 radially outward to facilitate contact between the skirt portion 38 and the wall 28 defining reservoir 22. The resilient material 58 also provides a radially compressive force that enhances the seal between the piston 26 and the interior wall 28. The resilient material 58 may, for example, include a thermoplastic elastomer or another suitable material.

Figure 5A:
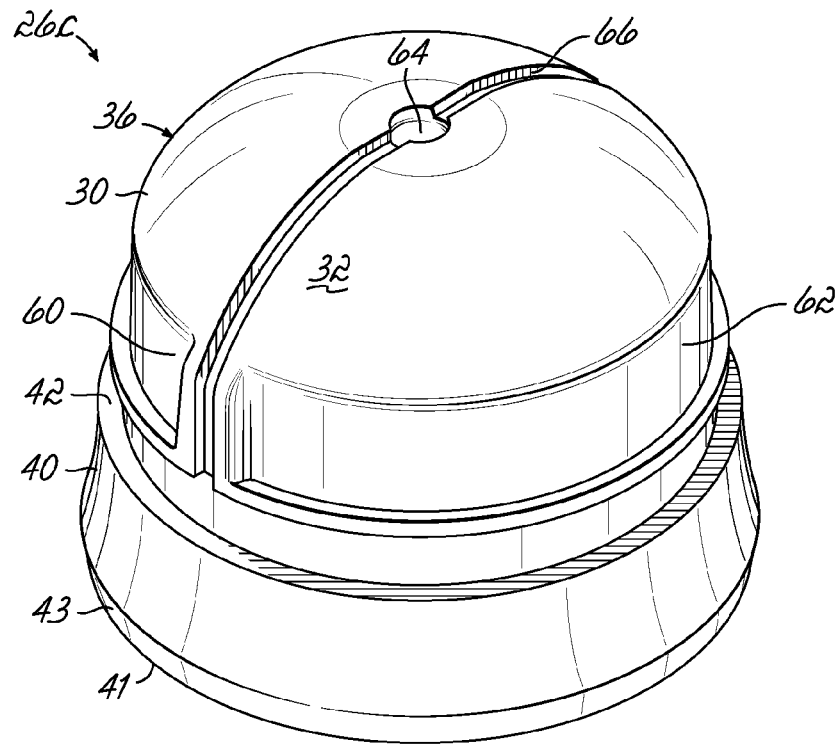
FIG. 5A is a perspective view of another embodiment of a piston.
Figure 5B:
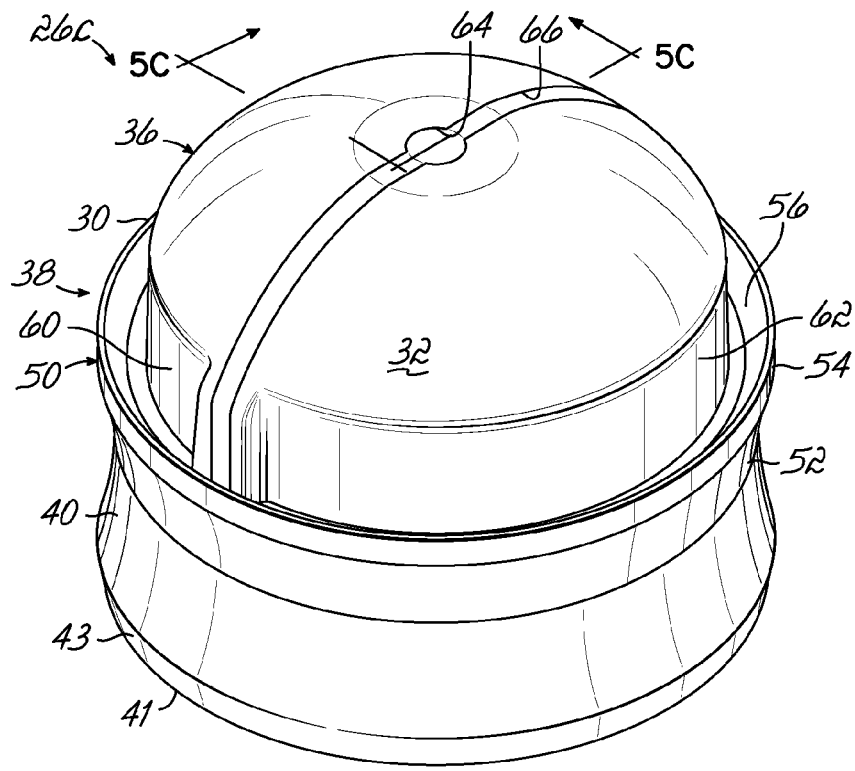
FIG. 5B is a perspective view similar to FIG. 5A including a skirt portion.
Figure 5C:
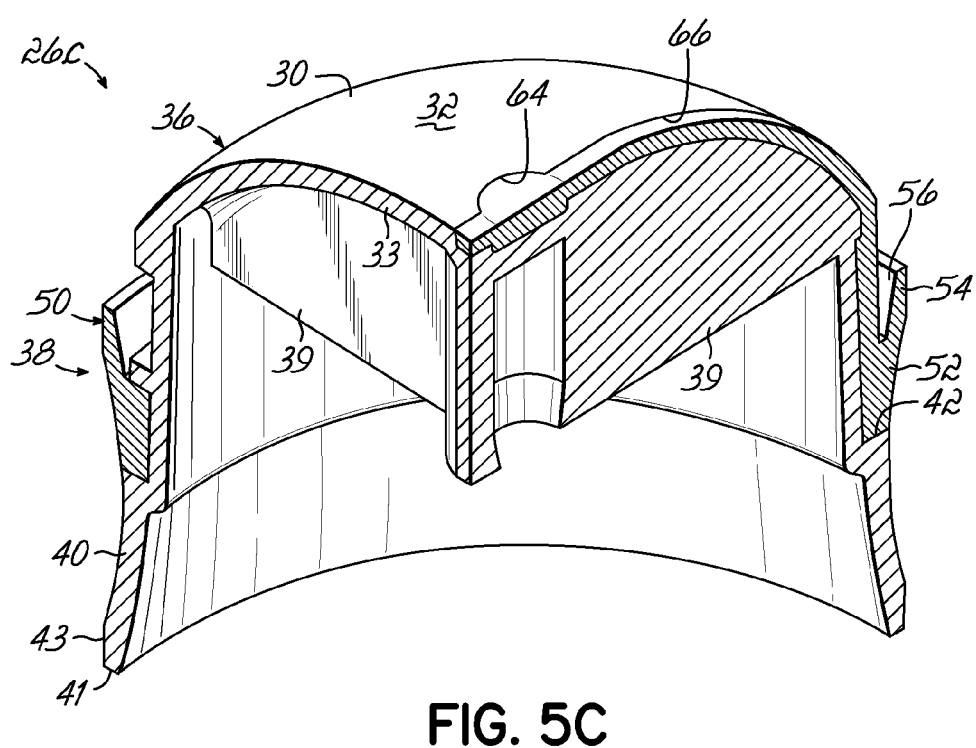
FIG. 5C is a cross-sectional view of the piston along line 5C-5C of FIG. 5B.

With reference to FIGS. 5A-5C, in which like reference numerals refer to like features of FIGS. 4A-4D, an embodiment of a piston 26c is similar in most respects to piston 26b of FIGS. 4A-4D, the description of which may be referred to for an understanding of piston 26c as well. Piston 26c includes a base portion 36 and a skirt portion 38, as well as a pair of circumferentially-directed recesses 60, 62 along sidewall 40 and adjacent head portion 30. Recesses 60, 62 prevent or minimize shrinkage of the piston 26c during cooling.

In one aspect of this embodiment, and by virtue of the two-part piston design, i.e., a relatively rigid base portion 36 and a relatively soft skirt portion 38, precise amounts of liquid may be dispensed while achieving the benefits of the softer skirt portion 38 (FIGS. 2A-2C) described above.

With reference to FIGS. 2A-5C, an exemplary embodiment of a method of making a piston 26 including one or more of the features described above (alone or in combination) for pistons 26, 26a, 26b, 26c will now be described. The piston 26 is formed by a two-shot molding operation wherein a first shot molds one of either the base portion 36 or the skirt portion 38, and wherein a second shot molds the other of the base portion 36 or skirt portion 38 so as to form the two-part piston 26 as a unitary structure. To this end, a mold (not shown) comprises first and second mold portions that may be assembled together to define an interior cavity having the general shape of the base portion 36. The base portion 36 is formed during the first shot of the two-shot molding operation by injecting a first curable material into the interior cavity to form base portion 36.

After the first curable material is injected into the mold to form the base portion 36, the second mold portion may be rotated such that the first and second mold portions thereby define another cavity for forming the skirt portion 38 on base portion 36. In alternate embodiments, the second mold portion may be removed and replaced with a third mold portion which is configured such that the first and third mold portions define a cavity for forming the skirt portion 38 of the piston 26.

A second curable material is injected into the newly formed cavity during the second shot of the two-shot mold operation to form the skirt portion 38 along the outer periphery of the base portion 36.

With continued reference to FIGS. 2A-5C, in one embodiment, a gate 64 for injecting the first and second curable materials may be centrally located through the outer surface 32 of head portion 30. In order to provide a flow path for the second curable material during the second shot of the molding operation, the base portion 36 may also include at least one cross channel 66 that extends from the gate 64 to the groove 42 where skirt portion 38 is formed. For instance, in FIGS. 2A and 4A, two such cross channels 66 are shown while in FIGS. 3A and 5A, one such cross channel 66 is shown. In this way, the second curable material is capable of flowing through the gate 64, through channel(s) 66 and into the groove 42 during the second shot of the molding operation. In addition, the gate 64 and the channel(s) 66 may also be filled with the second curable material during the second shot of the molding operation, thereby defining a strip in the head portion 30, partially defining the outer surface 32 thereof.

In a subsequent step, the finished piston 26 having the skirt portion 38 integrally molded to the base portion 36 is then removed from the mold. The piston 26 may then be disposed in the reservoir 22 of a dispenser 12 and used to dispense the liquid therefrom as described above.

In one aspect, the second curable material is adapted to have a hardness that is lower than the hardness of the first curable material. For instance, the first curable material may have a durometer hardness of about 65 Shore D or greater or between about 70 and about 80 Shore D, when cured, while the second curable material may have a durometer hardness of about 55 Shore D or less or between about 10 and about 50 Shore D when cured. An exemplary material for the first curable material may include polyethylene or polypropylene. An exemplary material for the second curable material may include thermoplastic elastomers (TPE), silicone based rubbers, fluoroelastomers such as Viton®, ethylene-propylene rubber (EPR), or buna-N (nitrile). Those of ordinary skill in the art will recognize that other suitable materials having the desired levels of hardness may be alternatively used.

Those of ordinary skill in the art will also recognize that while the molding process herein described includes a rotational mold, other molding processes may be alternatively used to achieve a two-part piston as described above. For example, the base portion 36 may be completely removed from the mold after forming thereof and placed in a separate mold for molding of the skirt portion 38. In addition, while the molding process described above formed the base portion 36 in the first shot and the skirt portion 38 in the second shot, it should be understood that the skirt portion 38 could have alternatively been molded in the first shot while the base portion 36 could have been molded in the second shot.

While the present invention has been illustrated by a description of various preferred embodiments and while these embodiments have been described in some detail, it is not intended to restrict or in any way limit the scope of the appended claims to such detail. For example, while the embodiments were shown and described for a syringe-type of dispenser, the two-part piston described herein may be beneficial in other types of dispensers. Thus, the term "liquid dispenser" as used herein is not limited to a syringe-type of dispenser but is intended to broadly represent any liquid dispenser having a piston that may benefit from the use of embodiments of the piston described above. Additional advantages and modifications will readily appear to those skilled in the art. The various features described above may be used alone or in numerous combinations depending on the needs and preferences of the user.

What is claimed is:

1. A method of making a piston for a dispenser adapted to dispense a liquid onto a substrate, comprising:
   molding a base portion of the piston by injecting a first curable material in a first shot of a molding operation, the base portion including a head portion having a central region and an outer surface and a generally tubular sidewall extending from the head portion to define an outer periphery of the base portion;
   forming at least one channel in the outer surface of the head portion and extending from the central region to the outer periphery during the first shot of the molding operation; and
   molding a skirt portion to the outer periphery of the base portion by injecting a second curable material through the at least one channel during a second shot of the molding operation.

2. The method of claim 1, wherein the first curable material has a first hardness, and the second curable material has a second hardness that is lower than the first hardness.

3. The method of claim 2, wherein injecting the first curable material further comprises injecting a curable material including a durometer hardness greater than or equal to about 65 Shore D.

4. The method of claim 2, wherein injecting the second curable material further comprises injecting a curable material including a durometer hardness less than or equal to about 55 Shore D.

5. The method of claim 2, wherein injecting the first curable material further comprises injecting at least one of polyethylene or polypropylene.

6. The method of claim 4, wherein injecting the second curable material further comprises injecting at least one of a group consisting of a thermoplastic elastomer (TPE), a silicone based rubber, a fluoroelastomer, an ethylene-propylene rubber (EPR), buna-N, and combinations thereof.

7. The method of claim 1, further comprising:
   filling the at least one channel with the second curable material.

8. The method of claim 1, further comprising:
   forming a circumferential groove in the generally tubular sidewall of the base portion during the first shot of the molding operation; and
   molding the skirt portion to the base portion along the circumferential groove.

9. A method of making a piston for a dispenser adapted to dispense a liquid onto a substrate and including a reservoir having a wall, the method comprising:
   molding a first portion of the piston by injecting a first curable material including a first hardness in a first shot of a molding operation, the first portion including an outer periphery; and
   molding a second portion of the piston to the first portion by injecting a second curable material including a second hardness during a second shot of the molding operation, the second hardness being different from the first hardness, the second portion being integrally molded with the outer periphery so as to define a skirt portion configured as a plurality of generally circumferential rings extending radially outward from the outer periphery and configured to engage the wall of the reservoir, each of the plurality of generally circumferential rings including a gap to define a labyrinth configured to allow air to move past the second portion through the labyrinth and configured to prevent the liquid from moving past the second portion.

10. The method of claim 9, wherein molding the first portion includes molding a base portion of the piston, and the second hardness is lower than the first hardness.

* * * * *